(12) United States Patent
Ramsey et al.

(10) Patent No.: US 11,291,459 B2
(45) Date of Patent: Apr. 5, 2022

(54) LATCHING WIRE CLIP

(71) Applicant: TELEFLEX MEDICAL INCORPORATED, Morrisville, NC (US)

(72) Inventors: Michael Dell Ramsey, Raleigh, NC (US); Carson J. Shellenberger, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 143 days.

(21) Appl. No.: 16/760,252

(22) PCT Filed: Oct. 29, 2018

(86) PCT No.: PCT/US2018/057966
§ 371 (c)(1),
(2) Date: Apr. 29, 2020

(87) PCT Pub. No.: WO2019/089440
PCT Pub. Date: May 9, 2019

(65) Prior Publication Data
US 2020/0352574 A1 Nov. 12, 2020

Related U.S. Application Data

(60) Provisional application No. 62/578,954, filed on Oct. 30, 2017.

(51) Int. Cl.
*A61B 17/122* (2006.01)
*A61B 17/00* (2006.01)
*A61B 17/12* (2006.01)

(52) U.S. Cl.
CPC .. *A61B 17/122* (2013.01); *A61B 2017/00871* (2013.01); *A61B 2017/12004* (2013.01)

(58) Field of Classification Search
CPC ..... A61B 17/08; A61B 17/083; A61B 17/122; A61B 17/1227; A61B 2017/12004; A61F 6/206
See application file for complete search history.

(56) References Cited

U.S. PATENT DOCUMENTS 243,629 A * 6/1881 Sanderson ................ B25B 9/02
294/99.2
1,236,282 A 8/1917 Fontaine
(Continued)

OTHER PUBLICATIONS

International Search Report from PCT/US2018/057966; dated Dec. 5, 2018.
(Continued)

*Primary Examiner* — Ryan J. Severson
(74) *Attorney, Agent, or Firm* — BakerHostetler

(57) ABSTRACT

A surgical clip may include a wire body having first and second free end portions. The surgical clip may also include first and second leg members connected by a hinge portion. The first leg member may include first and second segments of the wire body, the first segment may be spaced from the second segment, and the first and second free end portions may be disposed on a distal end portion of the first leg member. The second leg member may include third and fourth segments of the wire body, the third segment being spaced from the fourth segment. The hinge portion may join proximal end portions of the first and second leg members. The surgical clip may be movable between an open configuration and a closed configuration, wherein the second leg member is received between the first and second free end portions on the first leg member, and the first and second leg members pivot about the hinge portion to move the surgical clip between the open configuration and the closed configuration.

20 Claims, 7 Drawing Sheets

(56) References Cited

U.S. PATENT DOCUMENTS

| | | |
|---|---|---|
| 1,560,687 A | 11/1925 | Hauber |
| 2,060,724 A | 11/1936 | Carroll |
| 2,498,372 A | 2/1950 | Kortlucke, Jr. |
| 2,795,233 A * | 6/1957 | Zore .................. A45D 8/14 |
| | | 132/276 |
| 2,938,252 A | 2/1958 | Scheemaeker |
| 3,463,157 A | 8/1969 | Hunt |
| 3,996,937 A | 12/1976 | Williams |
| 4,024,868 A | 5/1977 | Williams et al. |
| 4,055,874 A * | 11/1977 | Brown .................. B42F 1/10 |
| | | 24/67.3 |
| 4,444,187 A | 4/1984 | Perlin |
| 4,658,822 A | 4/1987 | Kees, Jr. |
| 4,660,558 A | 4/1987 | Kees, Jr. |
| 4,834,096 A | 5/1989 | Oh et al. |
| 5,171,250 A | 12/1992 | Yoon |
| 5,217,473 A | 6/1993 | Yoon |
| 5,234,449 A | 8/1993 | Bruker et al. |
| 5,366,459 A | 11/1994 | Yoon |
| 5,487,746 A | 1/1996 | Yu et al. |
| 5,593,414 A | 1/1997 | Shipp et al. |
| 5,775,345 A * | 7/1998 | Chou .................. A45D 8/14 |
| | | 132/278 |
| 5,858,018 A | 1/1999 | Shipp et al. |
| 5,897,565 A | 4/1999 | Foster |
| 5,993,465 A | 11/1999 | Shipp et al. |
| 6,226,843 B1 | 5/2001 | Crainich |
| 6,241,740 B1 | 6/2001 | Davis et al. |
| 6,290,575 B1 | 9/2001 | Shipp |
| 6,293,956 B1 | 9/2001 | Crainich et al. |
| 6,305,387 B1 | 10/2001 | Atchison |
| 6,350,269 B1 | 2/2002 | Shipp et al. |
| 6,464,710 B1 | 10/2002 | Foster |
| 6,537,289 B1 | 3/2003 | Kayan et al. |
| 6,607,540 B1 | 8/2003 | Shipp |
| 6,652,545 B2 | 11/2003 | Shipp et al. |
| 7,207,997 B2 | 4/2007 | Shipp et al. |
| 7,338,503 B2 | 3/2008 | Rosenberg et al. |
| 7,572,266 B2 | 8/2009 | Young et al. |
| 7,582,095 B2 | 9/2009 | Shipp et al. |
| 7,678,125 B2 | 3/2010 | Shipp |
| 7,713,276 B2 | 5/2010 | Dennis |
| 7,776,058 B2 | 8/2010 | Rosenberg et al. |
| 8,075,576 B2 | 12/2011 | Eidenschink et al. |
| 8,172,870 B2 | 5/2012 | Shipp |
| 8,568,430 B2 | 10/2013 | Shipp |
| 8,945,151 B2 | 2/2015 | Salas |
| 9,326,772 B2 | 5/2016 | Rosenberg et al. |
| 9,445,820 B2 | 9/2016 | Whiting |
| 9,730,752 B2 * | 8/2017 | Keller .................. A61B 17/1285 |
| 10,828,041 B2 * | 11/2020 | Keller .................. A61B 17/128 |
| 2006/0100646 A1 | 5/2006 | Hart et al. |
| 2006/0212049 A1 | 9/2006 | Mohiuddin |
| 2007/0149988 A1 | 6/2007 | Michler et al. |
| 2007/0149989 A1 | 6/2007 | Santilli et al. |
| 2008/0045981 A1 | 2/2008 | Margolin et al. |
| 2008/0208324 A1 | 8/2008 | Glithero et al. |
| 2014/0243862 A1 | 8/2014 | Bagaoisan et al. |
| 2020/0352574 A1 * | 11/2020 | Ramsey .................. A61B 17/122 |

OTHER PUBLICATIONS

International Preliminary Report on Patentability and Written Opinion issued in PCT/US2018/057966, dated May 14, 2020.

* cited by examiner

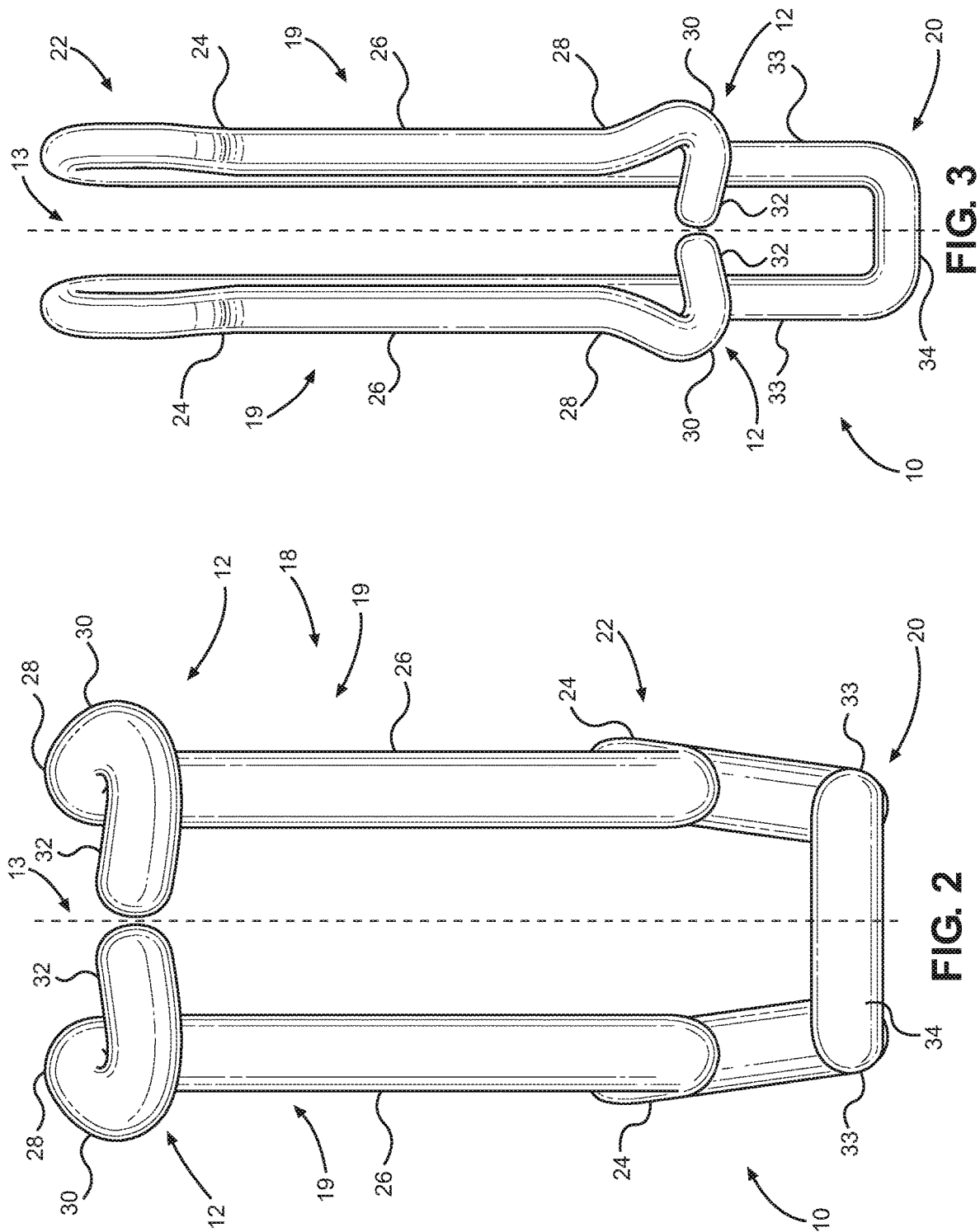

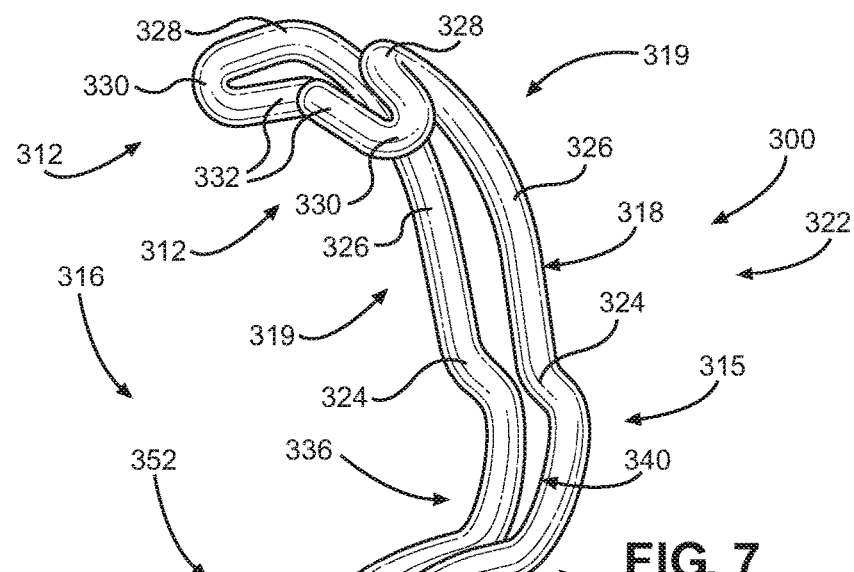
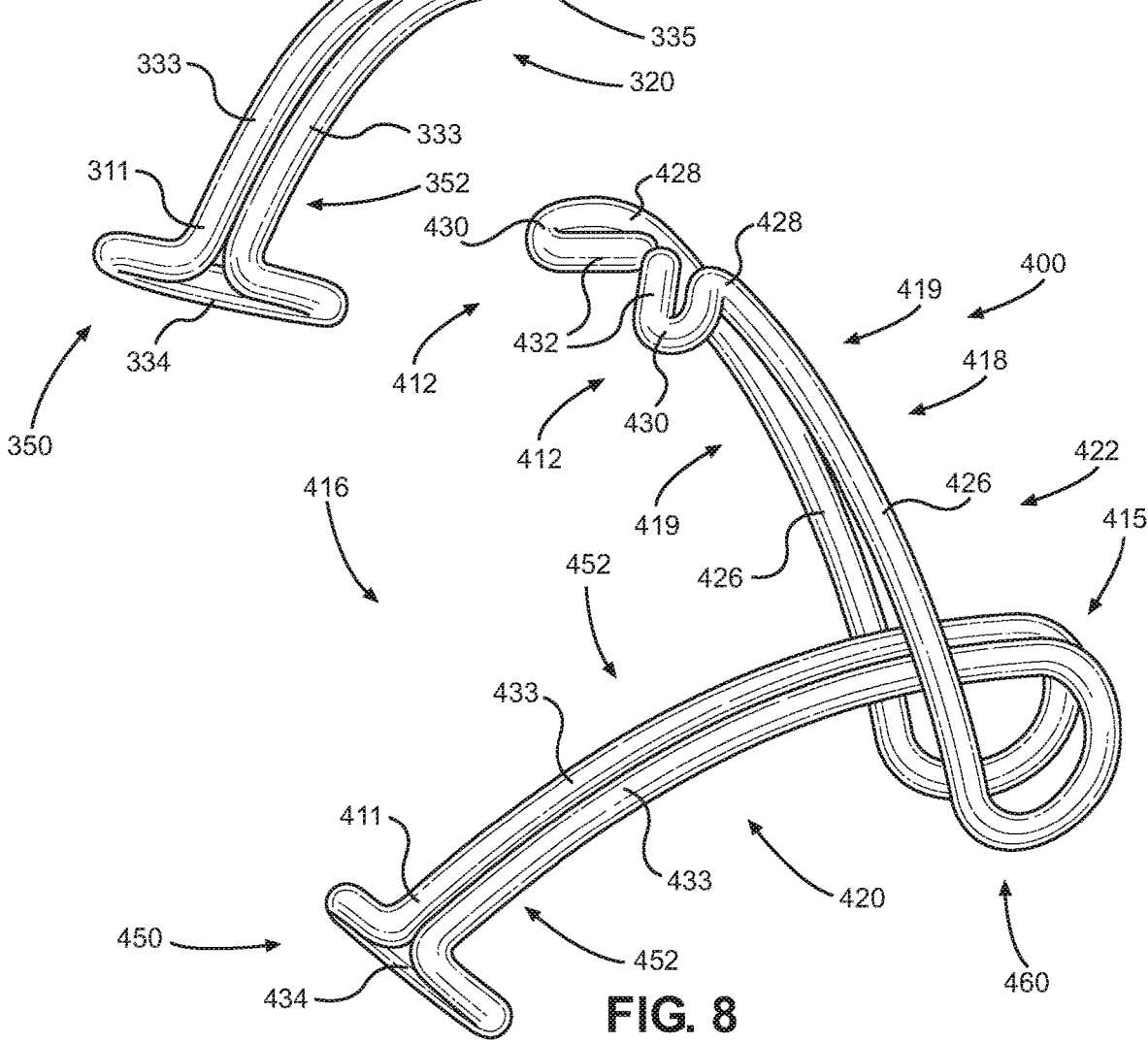

LATCHING WIRE CLIP

PRIORITY

This patent application is a national stage entry of PCT Application No. US2018/057966, filed on Oct. 29, 2018 and now expired, which claims priority to U.S. Provisional Patent Application No. 62/578,954, filed on Oct. 30, 2017 and now expired, the entire disclosure of which is incorporated herein by reference.

TECHNICAL FIELD

The present disclosure relates generally to medical devices, and more particularly to surgical clips for ligation of tissue.

BACKGROUND

The ligation of tissue (e.g., blood vessels, lymph nodes, nerves, fallopian tubes, or cardiac tissue) is a common practice of many surgical procedures. For example, temporarily ligating a blood vessel (e.g., veins or arteries) often facilitates the resection of aneurysmal tissue associated with the blood vessel. On the other hand, the ligation of fallopian tubes is often desired to be more permanent. In both cases, ligation clips have shown promise because they are relatively quick and easy to apply. Some of the current ligation clips are formed from a wire body.
Overview The present inventors recognize that there is a need to improve one or more features of the ligation clips. For example, the wire body of the ligation clip often functions by being biased into the closed configuration. This biasing feature adds complexity to the application by requiring an applier to maintain the clip in an open configuration during delivery. The biasing feature also minimizes the ability to provide differential pressure during application. For example, aneurysms may be prone to rupture if the tissue is abruptly compressed by a substantially large biasing force. It would be desirable to provide an improved ligation clip having a wire body with a latching mechanism. The disclosed apparatuses and methods are directed to mitigating or overcoming one or more of the problems set forth above and/or other problems in the prior art.

A first embodiment of the present disclosure is directed to a surgical clip configured to ligate tissue. The surgical clip may include a wire body having first and second free end portions. The surgical clip may also include a first leg member having a proximal end portion and a distal end portion. The first leg member may include first and second segments of the wire body, such that the first segment is spaced from the second segment, and the first and second free end portions are disposed on the distal end portion of the first leg member. The surgical clip may further include a second leg member having a proximal end portion and a distal end portion. The second leg member may include third and fourth segments of the wire body, such that the third segment is spaced from the fourth segment. The surgical clip may even further include a hinge portion joining the proximal end portions of the first and second leg members. The surgical clip may be movable between an open configuration where the distal end portions of the first and second leg members are spaced apart and a closed configuration where the second leg member is received between the first and second free end portions on the first leg member, and the first and second leg members pivot about the hinge portion to move the surgical clip between the open configuration and the closed configuration.

A second embodiment of the present disclosure is directed to a method of closing a surgical clip, the surgical clip may be formed from a wire body having first and second free end portions. The method may include moving a first leg member towards a second leg member from an open configuration to a closed configuration, the first and second free end portions being disposed on a distal end portion of the first leg member and a hinge portion joining proximal end portions of the first and second leg members. The method may also include receiving the second leg member between the first and second free end portions of the first leg member. The first leg member may include first and second segments of the wire body, the first segment being spaced from the second segment, and the second leg member may include third and fourth segments of the wire body, the third segment being spaced from the fourth segment.

BRIEF DESCRIPTION OF THE DRAWINGS

In order that the disclosure may be readily understood, aspects of this disclosure are illustrated by way of examples in the accompanying drawings.

FIG. 2 illustrates a longitudinal view of the first exemplary embodiment of the surgical clip of FIG. 1.

FIG. 3 illustrates a vertical view of the first exemplary embodiment of the surgical clip of FIGS. 1 and 2.

FIG. 7 illustrates an isometric view of a fourth exemplary embodiment of a surgical clip of the present disclosure.

FIG. 8 illustrates an isometric view of a fifth exemplary embodiment of a surgical clip of the present disclosure.

The same reference numbers are used in the drawings and the following detailed description to refer to the same or similar parts.

DETAILED DESCRIPTION

Figure 1:
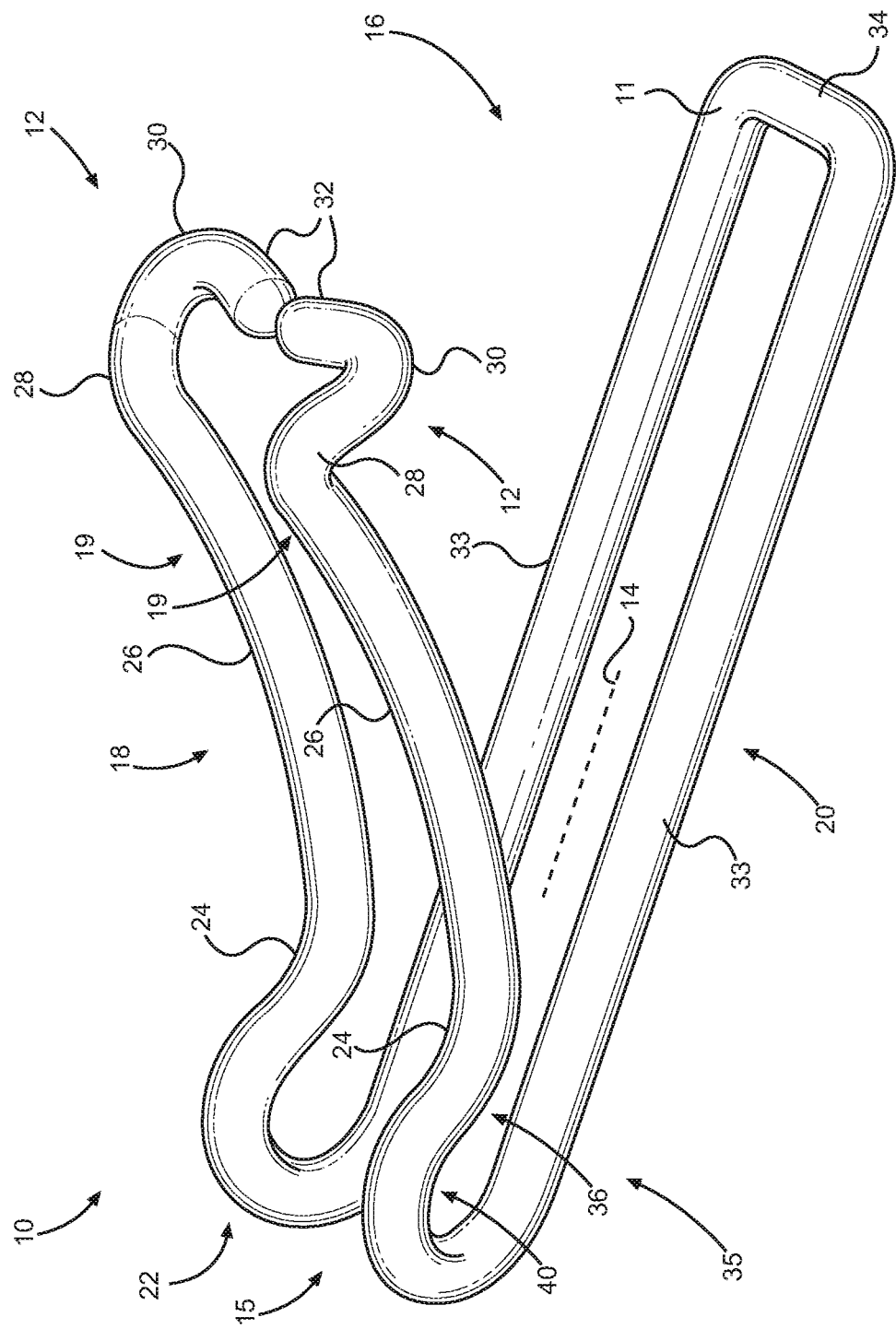
FIG. 1 illustrates an isometric view of a first exemplary embodiment of a surgical clip of the present disclosure.

The present disclosure is generally directed to a surgical clip configured to ligate tissue (e.g., a blood vessel). The surgical clip may include a first leg member, a second leg member, and a hinge portion, each of which may include two spaced segments of a wire body. In some embodiments, the wire body may extend continuously between a first free end portion and a second free end portion, spaced apart from each other. For example, a distal end portion of the first leg member may include the first and second free end portions of the wire body, such that the first leg member may be configured to receive a distal end portion of the second leg member therebetween in a latched configuration. The latching mechanism of the present disclosure may advantageously facilitate the releasable securement of the surgical clip without any additional steps of handling or compressing the latching mechanism. In some embodiments, the surgical clip may have a proximal pinching portion, for example, formed from a convex portion of the first leg member configuration to pinch a proximal end portion of the tissue to prevent tissue from slipping out of the surgical clip as the surgical clip closes. The surgical clip may be particularly useful as a hemostatic clip configured to be latched around a vessel to thereby reduce and/or stop the flow of fluid through the vessel.

The disclosure will now be described with reference to the figures, in which like reference numerals refer to like parts throughout. In accordance with conventional practice, as used herein, and unless otherwise indicated herein, the term "proximal end portion" refers to the specified end portion of the surgical clip or related component which is generally closer to the medical personnel handling or manipulating the device as it is intended to be used, and the term "distal end portion" shall refer to the specified end portion of the surgical clip or related component which is opposite the proximal end portion. As used herein, the term "longitudinal" is directed to the dimension which extends along the length of the surgical clip and/or related components, as would be commonly understood by one of skill in the art. Furthermore, as used herein, the "transverse" direction is directed to any axis or direction which is orthogonal to the longitudinal lengths of the surgical clip and/or related components.

FIG. 1 illustrates an elevated perspective view of an exemplary embodiment of a surgical clip 10, and FIGS. 2 and 3 illustrate longitudinal and vertical views of the surgical clip 10. As depicted, the surgical clip 10 may include a first leg member 18 and a second leg member 20 joined by a hinge portion 22. The surgical clip 10 may further include a proximal end portion 15 and a distal end portion 16. The distal end portion 16 may be configured to receive tissue (e.g., blood vessels, aneurysms, fallopian tubes, lymph nodes, nervous tissue, and umbilical cords) to be compressed and/or ligated. For example, the surgical clip 10 may be used in a method of closing the surgical clip 10 for surgical and/or non-surgical applications, as depicted in FIGS. 4A-E.

As further depicted in FIGS. 1-3, the surgical clip 10 may be formed of a single, unitary wire body 11 having first and second free end portions. The wire body 11 may have a cross-section including one of more of circular, round, ellipsoid, rectangular with rounded corners, square, rectangular, and/or polygonal segments. For example, as depicted in FIGS. 1-3, the surgical clip 10 may have a round and/or circular cross-section through substantially the entire length of the wire body 11. The wire body 11 may be deformed into a number of different configurations (e.g., an open configuration of FIG. 4A and a closed configuration of FIG. 4E). In some embodiments, the wire body 11 may extend continuously between the first and second free end portions 12. The term "continuous" may refer to a configuration of the wire body 11 having a substantially continuous cross-section extending throughout its length. For example, the term "continuous" may include embodiments of the wire body having variations, such as from a round cross-section to a rectangular cross-section with rounded corners. Round and/or the rectangular segments with rounded corners may advantageously reduce stress localizations on compressed tissue. The term "continuous" may also include the wire body 11 having turns and/or rounded free end portions 12, as depicted in FIGS. 1-3. The term "continuous" may further include embodiments of the wire body 11 having one or more notches or grooves 38 through the cross-section of the wire body 11 (as depicted in FIGS. 4A-4E), for example, to receive a clip applier. The term "continuous" may even further include embodiments of the wire body 11 including teeth and/or protrusions that may or may not interlock (not shown). However, the term "continuous" requires the non-adjacent segments of the wire body 11 to be substantially unconnected through substantially the entire length of the surgical clip 10. For example, as depicted in FIGS. 1-4E, the wire body 11 may be unconnected throughout the length of the first leg member 18. The continuous aspect of the wire body 11 may advantageously provide substantially uniform flexibility along the surgical clip 10 and a substantially uniform pressure distribution to compressed tissue. For example, the substantially uniform pressure distribution may reduce stress localizations on overstressed, fibrotic, and/or infarcted tissue. The term "continuous" does not preclude the free end portions 12 temporarily contacting each other, or being permanently joined similar to the second leg member 20.

However, it is also contemplated that the wire body 11 may be non-continuous, for example, wherein the lengths of the wire body 11 are joined by intermediate bridge members (not shown) to reinforce the surgical clip 10. In another example, the non-continuous wire body 11 may be formed from a single flat wire with discrete cut-out portions. In that sense, the components of the non-continuous embodiment may have spaced segments, but the spaced segments would not extend the length of the surgical clip 10.

It is contemplated that the surgical clip 10 may include continuous and non-continuous components. For example, in some embodiments, the hinge portion 22 may include one or more intermediate bridge members, while the wire body 11 of at least one of the first and second leg members 18, 20 may be continuous. In another example, the second leg member 20 may include one or more intermediate bridge members, while the wire body 11 of the first leg member 18 and/or hinge portion 22 may be continuous.

As depicted in FIGS. 1-3, the first leg member 18 may include first and second segments 19 of the wire body 11. The first and second segments 19 may be spaced along their lengths. For example, in continuous embodiments of the surgical clip 10, the first and second segments 19 may be spaced along the entire length of the first leg member 18, allowing substantial deflection of the segments 19. However, in non-continuous embodiments, the first and second segments 19 of the first leg member 18 may be joined by one or more intermediate bridge members (not shown). The first and second segments 19 may be symmetric about a central longitudinal plane 13 (depicted in FIGS. 2-3) extending through a central longitudinal axis 14 (depicted in FIG. 1). Each of the first and second segments 19 may include a convex portion 24, an elongated portion 26, and the free end portion 12. The convex portions 24 may be angled or curved relative to the central plane 13 and may enable pinching of the tissue, as the surgical clip 10 is initially compressed toward the close configuration, as further discussed below.

Each of the elongated portions 26 may extend from the convex portion 24 to the free end portion 12. In some embodiments, as depicted in FIGS. 1-3, the elongated portions 26 may be substantially parallel to each other in the open configuration, and each elongated portion 26 may have a slight curvature along a plane which is parallel to the central plane 13 of the surgical clip 10. However, in some embodiments, the elongated portions 26 may be slightly angled relative to each other (e.g., less than about 10 degrees) in the open configuration, such that the distal ends of the elongated portions 26 are spaced further than the proximal ends of the elongated portions 26. Nonetheless, the orientation of the portions 12, 24, 26 relative to the central plane 13 may change when the surgical clip 10 deforms from the open configuration to the closed configuration, as further depicted in FIGS. 4A-4E. It is contemplated that the elongated portions 26 of the first leg member 18 may be deflectable to conform to the compressed tissue when in the closed configuration (FIG. 4E).

The first and second free end portions 12 may be positioned on the distal ends of the elongated portions 26 and may be moveable relative to each other through the deflection of the elongated portions 26. One or more of the free end portions 12 may comprise a hook structure. For example, each of the free end portions 12 may include a hook structure comprising a first curved segment 28, a second curved segment 30, and a straight segment 32. As further depicted in FIG. 2, the first curved segment 28 may be curved away from the central plane 13 to a lateral position exterior of the second leg member 20. The second curved segment 30 may be positioned on the distal end of the first curved segment 28 and may be curved to end substantially perpendicular of the central plane 13, such that the free end portions 12 extend toward each other. The straight segments 32 may be on the distal ends of the second curved segments 30, and may be angled to provide a guiding surface for the spread of the free end portions 12 after initially contact with the second leg member 20, as depicted in FIGS. 4C-4D. As further depicted in FIG. 4E, once the free end portions 12 pass segments 33 of the second leg member 20, the free end portions 12 may move back toward each other due to the biasing of the wire body 11, and the segments 33 may settle within the first and second curved segments 28, 30 in the latched configuration. For example, the first free end portion 12 may extend around the first segment 33 of the second leg member 20, and the second free end portion 12 may extend around the second segment 33 of the second leg member 20. The biasing force of the wire body 11 may facilitate releasable latching of the surgical clip 10 and does not require any additional handling or compressing of the latching mechanism. The biasing force of the wire body 11 to the open configuration may further ensure contact between the free end portions 12 and the respective segments 33 of the second leg member 20 to prevent over compression by the leg members 18, 20.

The first and second segments 33 of the second leg member 20 may extend from the hinge portion 22 and may be connected by a closed segment 34. In some embodiments, the first and second segments 33 may be substantially straight and substantially parallel to each other along the central plane 13 of the surgical clip 10. However, in some embodiments, the first and second segments 33 may be curved and/or angled relative to each other. The first and second segments 33 may respectively engage the first and second free end portions 12 to releasably secure the surgical clip 10 in a latched configuration, for example, by the free end portions 12 extending around opposing sides of the leg member segments 33 (FIG. 4E). In continuous embodiments of the surgical clip 10, the segments 33 may be spaced along substantially the entire length of the first leg member. However, in non-continuous embodiments, the segments 33 of the second leg member 20 may be joined, for example, by intermediate bridge members (not shown).

The hinge portion 22 may be configured to pivot the first leg member 18 relative to second leg member 20, or vice versa. For example, the hinge portion 22 may include one or more deflectable portions that enable relative movement between the first leg member 18 and the second leg member 20. The hinge portion 22 may deform in more than one direction as the surgical clip 10 transitions from the open configuration (FIG. 4A) to the closed configuration (FIG. 4E), For example, the segments of the hinge portion 22 may spread away from the central plane 13 as the free end portions 12 spread around the segments 33 of the second leg member 20 (FIGS. 4C-4D). Furthermore, slight spreading of the segments of the hinge portion 22 may occur prior to the free end portions 12 initially contacting the segments 33 of the second leg member 20 (FIG. 4A-4C), due to a bowing effect. The spreading of the hinge portion 22 may also cause spreading of the elongated portions 26 of the first leg member 18 and/or the segments 33 of the second leg member 20.

The hinge portion 22 may also define at least a portion of a pinching area 35 configured to enhance security of the tissue and/or reduce the potential of tissue squeezing out of the surgical clip 10 as the surgical clip 10 closes. The pinching area 35 may include a narrow opening 36 and a wider opening 40 at least partially defined by the convex portions 24 of the first lea member 18 and the segments 33 of the second leg member 20. The pinching of the convex portions 24 may enable the surgeon to manipulate (e.g., pinch and pull) the tissue as the surgical clip 10 is in a substantially open configuration (e.g., FIG. 4B). For example, if tissue is proximate to other bodily structures, the surgeon may pinch and retract the tissue away from the other structures to prevent the other structures from interfering with the ligation and/or to prevent the latching mechanism from damaging the other structures. The initial pinching of tissue may also aid in skeletonizing tissue prior to closure. The pinching may further enhance security of the tissue as the remaining portion of the surgical clip 10 is closed, such that the tissue does not squeeze out of the distal end portion 16 as the surgical clip 10 closes. For example, a proximal end portion of the tissue may be retained within the narrow opening 36 and/or the wider opening 40 by initial compression of the convex portion 24 (FIG. 4A-4B), while the elongated portion 26 is applied to the remaining length of tissue (FIG. 4B-4E).

The surgical clip 10 may be made of any suitable size to be applied to any number of tissues, such as blood vessels, aneurysms, fallopian tubes, lymph nodes, nervous tissue, and umbilical cords. The surgical clip 10 may be constructed from any suitable permanent or resorbable material (e.g., metals or polymers), such as spring steel or Nitinol. The surgical clip 10 may be biased in the open configuration (FIG. 4A), such that the surgical clip 10 is releasably secured in the latched configuration (FIG. 4E). The biasing of the wire body 11 may be provided by the resilient nature of spring steel or the shape memory of Nitinol. For example, the segments 19 of the first leg member 18 may be biased to the spacing of the open configuration, such that the free end portions 12 are releasably secured around the segments 33 of the second lea member 20. Furthermore, the biasing of the first and second leg members 18, 20 to the open configuration may reduce over-compression of the tissue. For example, the leg members 18, 20 may be retained in a spaced configuration to accommodate the compressed tissue in the latched configuration. The latched spacing between the leg members 18, 20 may be modified to accommodate different sized tissue, for example, by adjusting the dimensions of the free end portions 12.

FIGS. 4A-4E illustrate a series of exemplary configurations or an exemplary method of closing the surgical clip 10, for example, to compress and/or ligate tissue. The method may be performed by pivoting the first leg member 18 relative to the second leg member 20 from an open configuration (FIG. 4A) to a closed and/or latched configuration (FIG. 4E). The surgical clip 10 may be applied with a manual or automatic clip applier. For example, the surgical clip 10 may be applied by pivoting jaws of a manual clip applier that engages a notch or groove 38 on each of the segments 19 of the first leg member 18. The surgical clip 10 may be biased into the open configuration (FIG. 4A), such that pressure would be applied by the clip applier to compress the surgical clip 10.

Figure 4A:
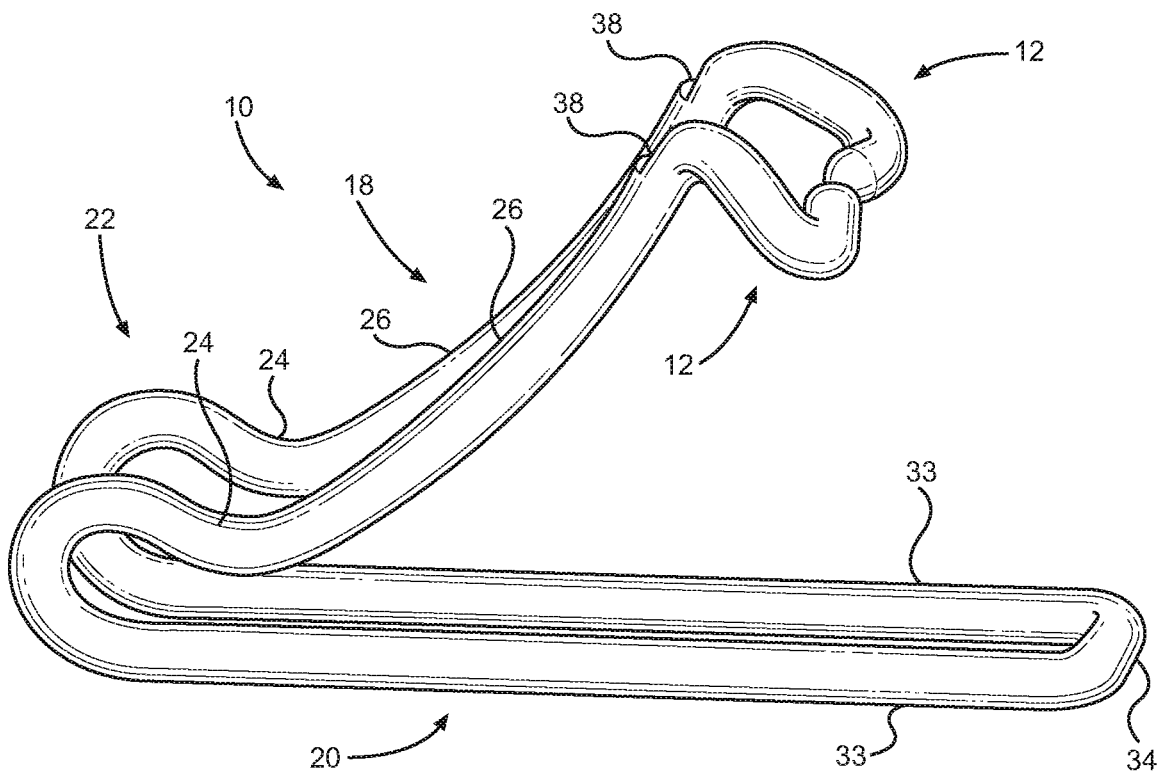
FIGS. 4A-4E illustrate a method of closing the first exemplary embodiment of the surgical clip of FIGS. 1-3.
Figure 4B:
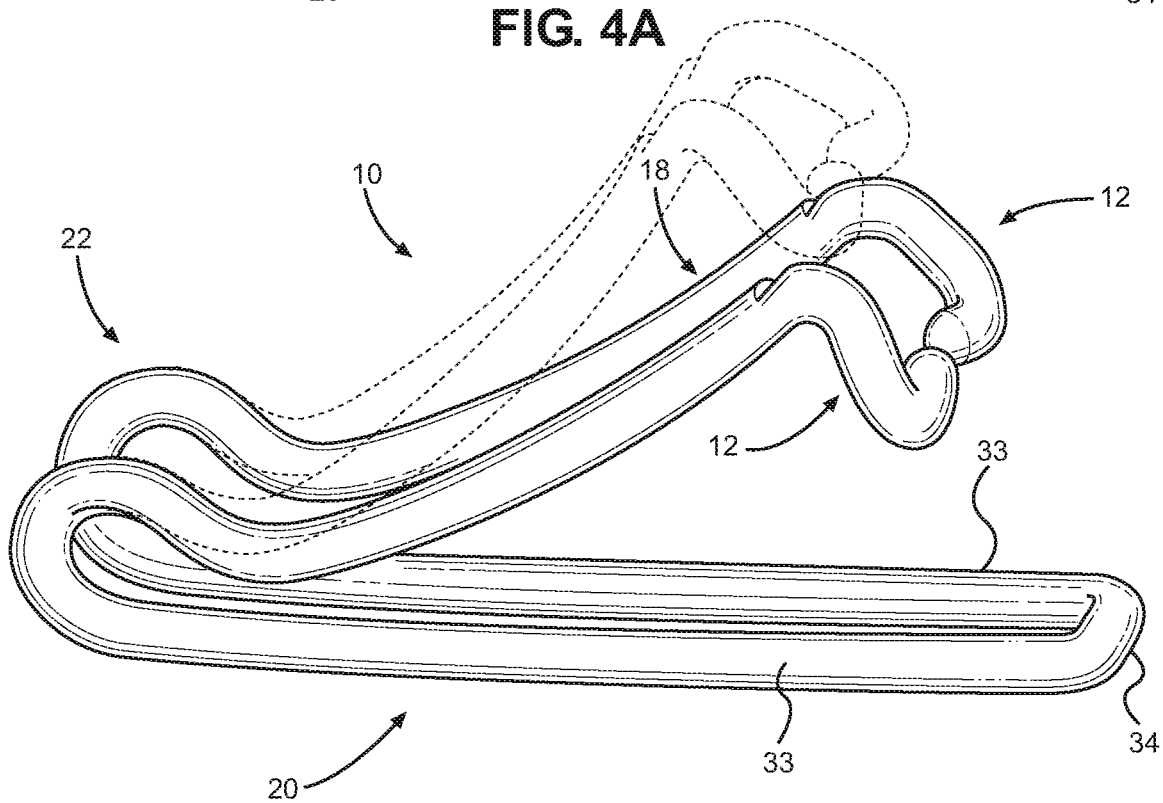
Figure 4C:
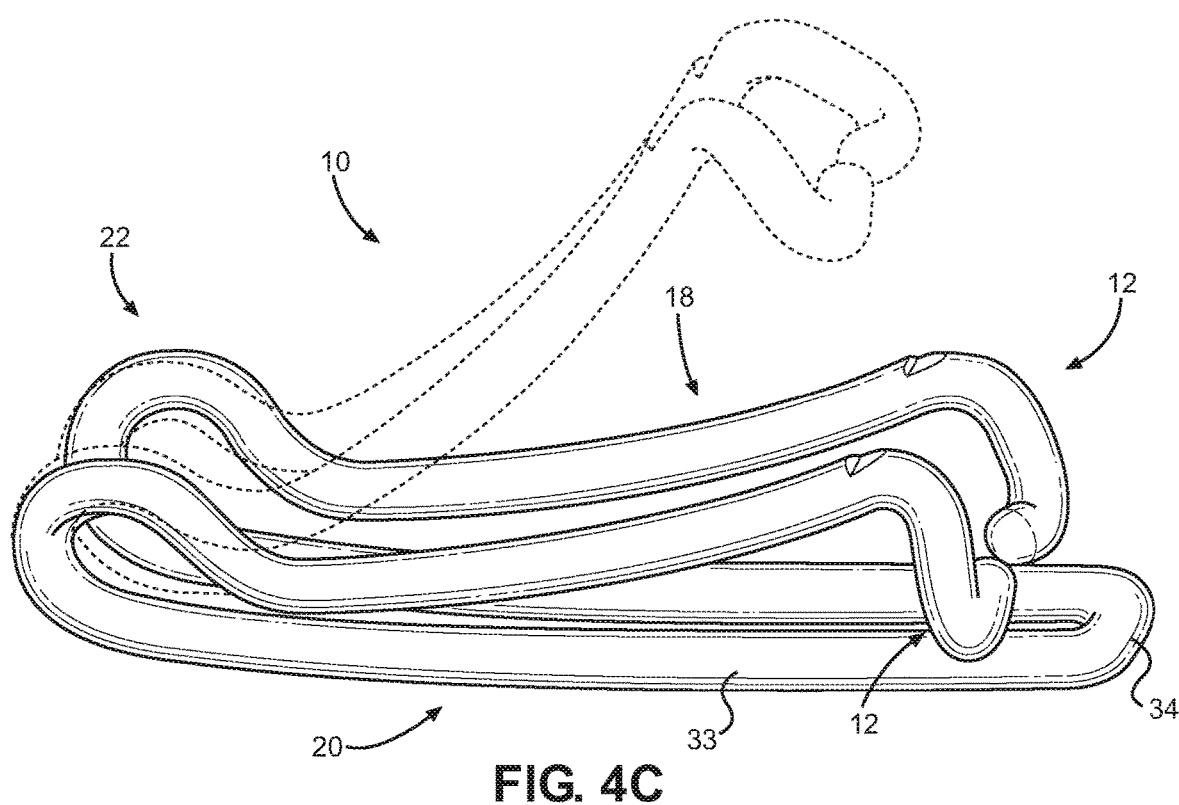
Figure 4D:
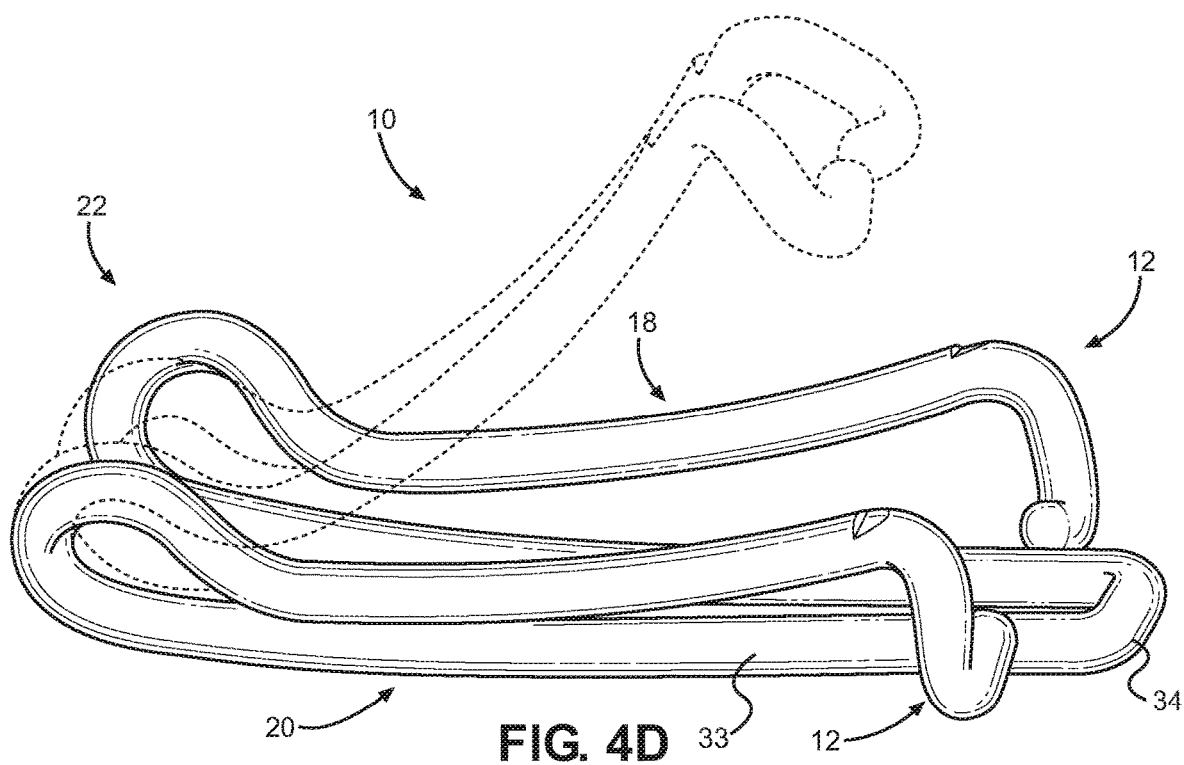
Figure 4E:
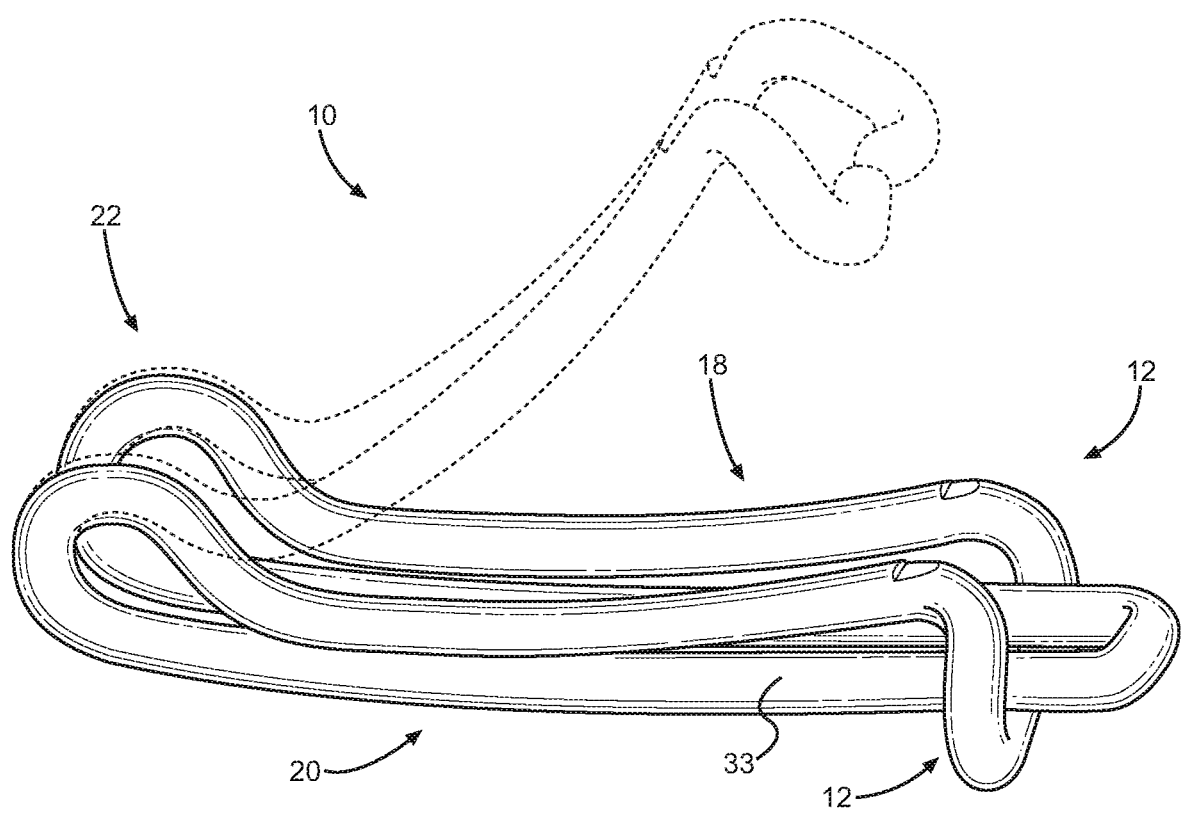

FIG. 4B illustrates (in solid lines), the surgical clip 10 being initially compressed from the open configuration (FIG. 4A). The first leg member 18 may pivot about the hinge portion 22 and/or the convex portion 24 as the surgical clip 10 is compressed. In some embodiments, the surgical clip 10 may be applied by compressing one or more of the first and second leg members 18, 20 toward each other. It is contemplated that the segments of one or more of the first leg member 18, the second leg member 20, and the hinge portion 22 may slightly spread as the surgical clip 10 is compressed due to a bowing force of the wire body 11.

FIG. 4C illustrates (in solid lines) the free end portions 12 initially contacting the segments 33 of the second leg member 20. FIG. 4D illustrates (in solid lines) the free end portions 12 deflecting around the segments 33 of the second leg member 20 to the closed and/or latched configuration (FIG. 4E). In some embodiments, the deflection of the free end portions 12 may be due to the contact of the straight segments 32 with the segments 33 of the second leg member 20. Once the free end portions 12 pass the segments 33 of the second leg member 20, the free end portions 12 may move toward each other due to a biasing force of the wire body 11, and the segments 33 may settle within the first and second curved segments 28, 30 in the latched configuration (FIG. 4E). The biasing of the wire body 11 to the open configuration (FIG. 4A) may releasably secure the surgical clip 10 in the latched configuration (FIG. 4E) and prevent over compression of the tissue. It is also noted that the open configuration of the surgical clip 10 is illustrated as dashed lines in FIGS. 4B-4E.

It is also contemplated the surgical clip 10 may be released from the latched configuration (FIG. 4E), for example, when it is desired to either remove and/or reposition the surgical clip 10. The surgical clip 10 may be released by advancing the first leg member 18 slightly toward the second leg member 20 and spreading the free end portions 12 of the first leg member 18 to clear the segments 33 of the second leg member 20. The first and/or second leg member 18, 20 may then be moved away from each other to the open configuration (FIG. 4A).

Figure 5:
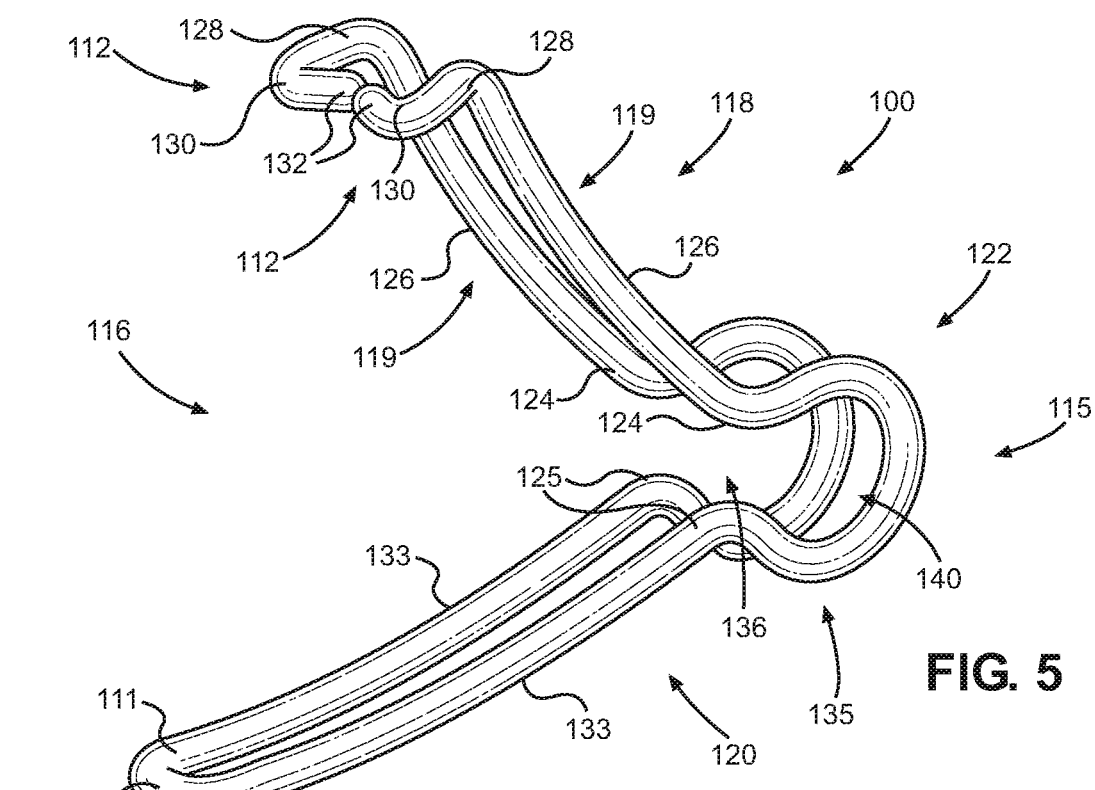
FIG. 5 illustrates an isometric view of a second exemplary embodiment of a surgical clip of the present disclosure.

FIG. 5 illustrates a second embodiment of a surgical clip 100 of the present disclosure. The surgical clip 100 may include a first leg member 118, a second leg member 120, and a hinge portion 122, each of which may include two spaced segments 119 of a wire body 111. For the sake of brevity, features similar to those of the surgical clip 10 may not be discussed with reference to surgical clip 100.

As illustrated, the hinge portion 122 may form a pinching area 135 configured to enhance security of the tissue and/or reduce the potential of tissue squeezing out of the surgical clip 100 as the surgical clip 100 closes. The hinge portion 122 may include first convex portions 124 on the proximal end of the first leg member 118 and second convex portions 125 on a proximal end of the second leg members 120. The first and second convex portions 124, 125 may form a narrow opening 136 configured to provide improved securement of tissue therebetween. For example, tissue may be received into the narrow opening 136 and pinched by the convex portions 124, 125 in the open configuration, as illustrated in FIG. 5. In some embodiments, the convex portions 124, 125 may be sized to pinch the tissue when the surgical clip 100 is compressed slightly while the distal ends of the first and second leg members remain spaced apart. The pinching of the convex portions 124, 125 may further enhance security of the tissue as the remaining portion of the surgical clip 100 is closed, such that the tissue does not squeeze out of the distal end portion 116 as the surgical clip 100 closes. The surgical clip 100 may also be configured to manipulate (e.g., pull and/or retract) the tissue while in a substantially open configuration.

Figure 6:
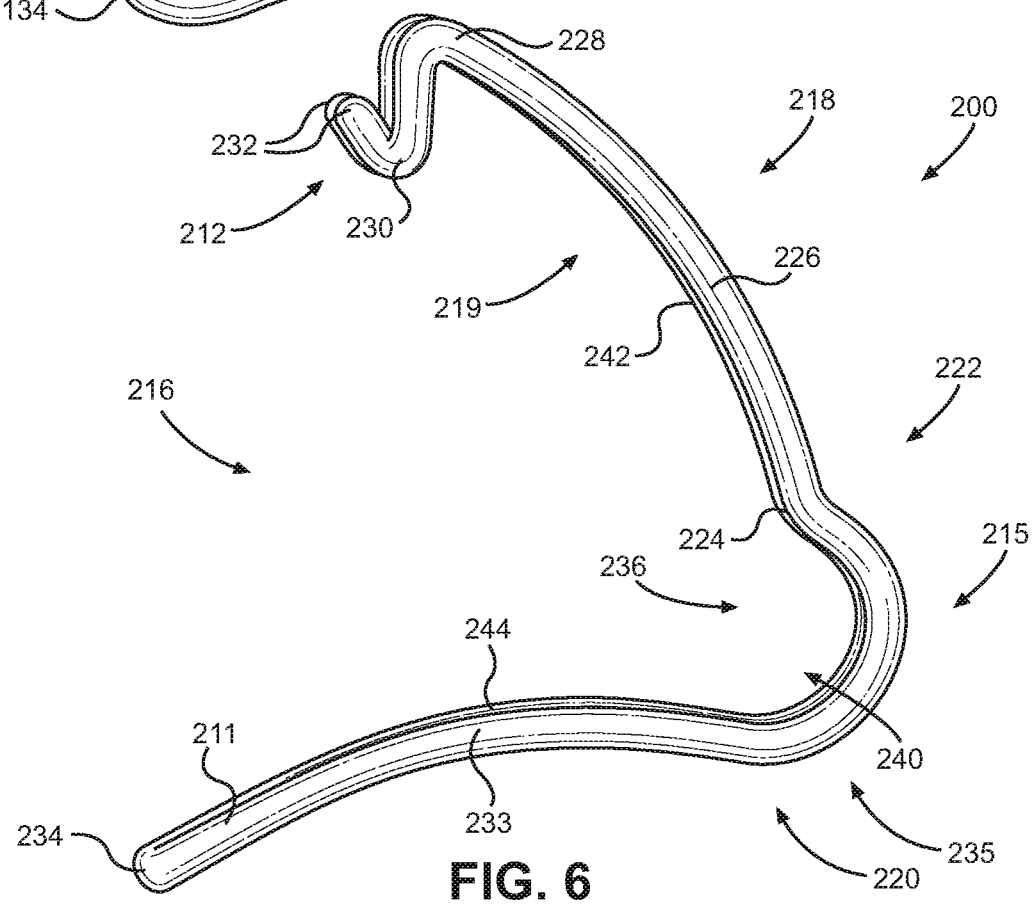
FIG. 6 illustrates a side view of a third exemplary embodiment of a surgical clip of the present disclosure.

FIG. 6 illustrates a third embodiment of a surgical clip 200 of the present disclosure. The surgical clip 200 may include a first leg member 218, a second leg member 220, and a hinge portion 222, each of which may include two spaced segments 219 of a wire body 211. For the sake of brevity, features similar to those of at least one of the surgical clips 10, 100 may not be discussed with reference to surgical clip 200.

As illustrated, the first leg member 218 may include a convex portion 224 and a concave portion 242 along each of the elongated portions 226, and the second leg member 220 may include a convex portion 244 along each of the segments 233. The concave portions 242 may have a curvature that corresponds to the convex portions 244, such that the concave portions 242 receive the convex portions 244 in a closed configuration and provide a favorable compression of tissue therebetween.

FIG. 7 illustrates a fourth embodiment of a surgical clip 300 of the present disclosure. The surgical clip 300 may include a first leg member 318, a second leg member 320, and a hinge portion 322, each of which may include two spaced segments 319 of a wire body 311. For the sake of brevity, features similar to those of at least one of the surgical clips 10, 100, 200 may not be discussed with reference to surgical clip 300.

As illustrated, the second leg member 320 may include a distal end portion 350 that is wider than a proximal portion 352. The distal end portion 350 may be substantially the same width as the hook structures on the distal end of the first leg member 318. The widened distal end portion 350 may engage the hook structures in a closed configuration, further retaining the surgical clip 300. As further illustrated, the first leg member 318 may include a convex portion 324 and a concave portion along each of the elongated portions 326, and the second leg member 320 may include a convex portion along each of the segments 333. The concave portions may have a curvature that corresponds to the convex portions, such that the concave portions receive the convex portions in a closed configuration and provide a favorable compression of tissue therebetween.

FIG. 8 illustrates a fifth embodiment of a surgical clip 400 of the present disclosure. The surgical clip 400 may include a first leg member 418, a second leg member 420, and a hinge portion 422, each of which may include two spaced segments 419 of a wire body 411. For the sake of brevity, features similar to those of at least one of the surgical clips 10, 100, 200, 300 may not be discussed with reference to surgical clip 400.

As illustrated, the hinge portion 422 may include a closed loop 460 providing an increased biasing force to the open configuration of the surgical clip 400. The increased biasing force may improve the securement of the surgical clip 400 in the latched configuration. As further illustrated, the second leg member 420 may include a distal end portion 450 that is wider than a proximal portion 452. The distal end portion 450 may be substantially the same width as the hook structures on the distal end of the first leg member 418. The widened distal end portion 450 may engage the hook structures in a closed configuration, further retaining the surgical clip 400.

The many features and advantages of the disclosure are apparent from the detailed specification, and thus, it is intended by the appended claims to cover all such features and advantages of the disclosed embodiments which fall within the true spirit and scope of the disclosure. Further, since numerous modifications and variation will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A surgical clip including a wire body having first and second free end portions, the surgical clip comprising:
    a first leg member having a proximal end portion and a distal end portion, the first leg member including first and second segments of the wire body, the first segment being spaced from the second segment, and the first and second free end portions being disposed on the distal end portion of the first leg member;
    a second leg member having a proximal end portion and a distal end portion, the second leg member including third and fourth segments of the wire body, the third segment being spaced from the fourth segment; and
    a hinge portion joining the proximal end portions of the first and second leg members,
    wherein the surgical clip is movable between an open configuration where the distal end portions of the first and second leg members are spaced apart and a closed configuration where the second leg member is received between the first and second free end portions on the first leg member, the first leg member being configured to pivot relative to the second leg member about the hinge portion to move the surgical clip between the open configuration and the closed configuration.

2. The surgical clip of claim 1, wherein the wire body includes a round cross-section through substantially the entire length of the wire body.

3. The surgical clip of claim 1, wherein the wire body is a single, unitary body extending continuously between the first and second free end portions.

4. The surgical clip of claim 1, wherein the first and second free end portions are configured to spread out when receiving the second leg member.

5. The surgical clip of claim 1, wherein the first free end portion comprises a first hook, the second free end portion comprises a second hook, and the first and second hooks are configured to releasably secure the surgical clip in the closed configuration.

6. The surgical clip of claim 5, wherein the first hook is configured to latch around the third segment, and the second hook is configured to latch around the fourth segment.

7. The surgical clip of claim 5, wherein each of the first and second hooks comprises a first segment curved in a first direction and a second segment curved in a second direction.

8. The surgical clip of claim 5, wherein each the first and second hooks further comprises a straight segment.

9. The surgical clip of claim 1, wherein the third and fourth segments are substantially parallel in the closed configuration.

10. The surgical clip of claim 1, wherein the third and fourth segments are connected at the distal end portion of the second leg member.

11. The surgical clip of claim 1, wherein the first segment is unconnected to the second segment through the entire length of the first leg member.

12. The surgical clip of claim 1, wherein the first leg member comprises a convex portion configured to pinch tissue received between the first and second leg members.

13. The surgical clip of claim 12, wherein the convex portion of the first leg member is configured to pinch the tissue against a straight section of the second leg member.

14. The surgical clip of claim 1, wherein the surgical clip is symmetric about a central longitudinal plane.

15. The surgical clip of claim 1, wherein the surgical clip is biased into the open configuration.

16. A method of closing a surgical clip formed from a wire body having first and second free end portions, the method comprising:
    moving a first leg member towards a second leg member from an open configuration to a closed configuration, the first and second free end portions being disposed on a distal end portion of the first leg member and a hinge portion joining proximal end portions of the first and second leg members; and
    receiving the second leg member between the first and second free end portions of the first leg member in the closed configuration,
    wherein the first leg member includes first and second segments of the wire body, the first segment being spaced from the second segment, and the second leg member includes third and fourth segments of the wire body, the third segment being spaced from the fourth segment.

17. The method of claim 16, wherein the wire body includes a round cross-section through substantially the entire length of the wire body.

18. The method of claim 16, wherein the wire body extends continuously between the first and second free end portions.

19. The method of claim 16, further comprising spreading out the first and second free end portions when the second leg member is received between the first and second free end portions.

20. The method of claim 16, further comprising releasably securing the first and second leg members together with first and second hooks, wherein the first free end portion comprises the first hook and the second free end portion comprises the second hook.

* * * * *